United States Patent [19]
Sederholm

[11] Patent Number: 5,658,294
[45] Date of Patent: Aug. 19, 1997

[54] INSTRUMENT FOR HOLDING AN ACETABULAR CUP

[75] Inventor: Gary W. Sederholm, Austin, Tex.

[73] Assignee: Sulzer Orthopedics Inc., Austin, Tex.

[21] Appl. No.: 595,422

[22] Filed: Feb. 5, 1996

Related U.S. Application Data

[63] Continuation of Ser. No. 161,678, Dec. 2, 1993, abandoned.

[51] Int. Cl.⁶ .................................................. A61B 17/58
[52] U.S. Cl. ........................... 606/91; 606/99; 623/18; 623/22
[58] Field of Search ........................ 606/91, 99; 623/16, 623/18, 22; 403/132, 133, 135; D24/133, 140, 145

[56] References Cited

U.S. PATENT DOCUMENTS

| | | | |
|---|---|---|---|
| 3,829,904 | 8/1974 | Ling et al. | 623/22 |
| 4,305,394 | 12/1981 | Bertuch, Jr. | 606/91 |
| 4,871,368 | 10/1989 | Wagner | 623/22 |
| 5,037,424 | 8/1991 | Aboczsky | 606/91 |
| 5,061,270 | 10/1991 | Aboczky | 606/91 |

FOREIGN PATENT DOCUMENTS 0535973  4/1993  European Pat. Off. ............... 606/91

Primary Examiner—Michael Buiz
Assistant Examiner—Mark S. Leonardo
Attorney, Agent, or Firm—Richard L. Robinson

[57] ABSTRACT

An instrument for holding an acetabular cup. An elongate hollow tubular member has a proximal end and a distal end and a generally transverse end face at the distal end. A pair of pins extend axially outwardly from the transverse end face. An elongate rod is mounted within the elongate hollow tubular member for axial movement relative thereto. A ball is attached to one end of the elongate rod proximate the transverse end face and is moveable together with the elongate rod. The ball has a spherical surface for engaging a portion of the inner bearing surface of an acetabular cup that extends radially inwardly relative to the polar axis of the acetabular cup. Retraction of the ball toward the end face of the tubular member draws the cup toward the end face. Corresponding holes in the rim of the cup receive the pins to prevent lateral movement of the cup on the end face of the instrument.

10 Claims, 5 Drawing Sheets

INSTRUMENT FOR HOLDING AN ACETABULAR CUP

This is a continuation of application Ser. No. 08/161,678 filed on Dec. 2, 1993 now abandoned.

BACKGROUND OF THE INVENTION

The present invention relates generally to implantable orthopedic hip prostheses and more particularly to an instrument for holding an acetabular cup to facilitate orientation of the cup during cemented implantation.

BACKGROUND INFORMATION

A total hip prostheses includes a femoral component and an acetabular cup component. The femoral component has a stem for receipt and fixation within the femoral canal at a resected proximal end of the femur and has a spherical head that may be integral with or removably attached to the stem. The acetabular cup has an outer, generally spherical surface for receipt within a reamed acetabulum and has an inner bearing cavity for receiving the head of the femoral component. The head articulates relative to the bearing cavity such that the total hip prosthesis restores a normal range of motion to an otherwise diseased or damaged hip joint.

One known general configuration for an acetabular cup involves a one-piece cup and bearing made of a biocompatible plastic such as high-density polyethylene. The cup has a generally hemispherical shape, defined by a generally hemi-spherical outer surface and a generally hemi-spherical inner bearing surface. One known variation involves a hood extending from the face of the cup adjacent the bearing cavity which accommodates a bearing cavity having an axis that is inclined relative to the axis of the cup.

One-piece all-polyethylene acetabular cups are designed to be implanted within the acetabulum and secured with bone cement. It is desirable to provide instrumentation for holding the acetabular cup during implantation and for ensuring that the cup is properly orientated relative to the body axes of the patient prior to the cement hardening.

The present invention provides as instrument that securely holds an acetabular cup during implantation and provides for ease of orientation.

SUMMARY OF THE INVENTION

According to one aspect of the present invention, there is provided an instrument for holding an acetabular cup. The instrument includes an elongate hollow tubular member having a proximal end and a distal end and a generally transverse end face at the distal end thereof. At least one pin extends axially outwardly from the transverse end face. An elongate rod is mounted within the elongate hollow tubular member for axial movement relative thereto. A ball is attached to one end of the elongate rod proximate the transverse end face and is moveable together with the elongate rod. The ball has a spherical surface, at least a portion of which faces the end face of the tubular member.

It is an object of the present invention to provide an improved instrument for holding an acetabular cup. Other objects and advantages of the present invention will be apparent from the following description of a preferred embodiment made with reference to the drawings.

DETAILED DESCRIPTION OF A PREFERRED EMBODIMENT

Figure 1:
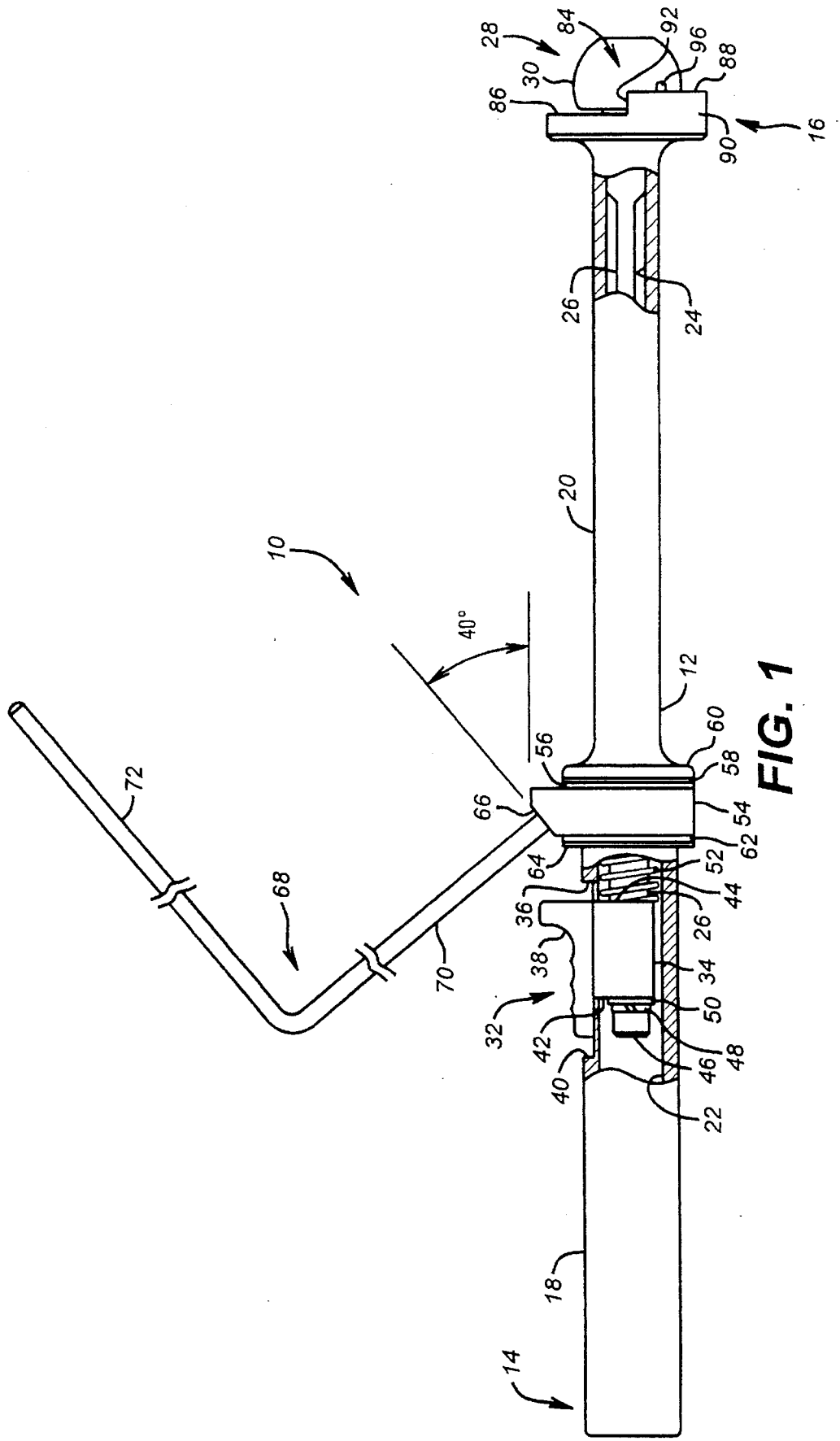
FIG. 1 is a side view of an instrument for holding an acetabular cup configured in accordance with the present invention, shown partially in section.

Referring to FIG. 1, an instrument 10 is illustrated that is configured in accordance with the present invention. Instrument 10 includes an elongate hollow tubular member 12 having a proximal end 14 and a distal end 16. Tubular member 12 can be considered as having two portions, a proximal handle 18 and a distal neck 20. Handle 18 is of somewhat greater diameter than neck 20. Tubular member 12 is preferably hollow throughout its length and open at both ends. The inner diameter 22 of handle 18 is greater than the inner diameter 24 of neck 20.

A rod 26 is disposed within tubular member 12 and extends throughout the length of neck 20 and extends partially within handle 18. The distal end of rod 26 extends beyond the open distal end 16 of tubular member 12 and is affixed to a ball 28 having a spherical surface 30. Rod 26 is mounted in sliding engagement with the inner diameter of neck 20 to permit axial movement of rod 26 relative to tubular member 12. Ball 28 is fixed to rod 26 so as to move therewith.

An actuator 32 has a main body 34 disposed within handle 18 and affixed to the proximal end of rod 26, preferably by threaded engagement. The threaded connection between the proximal end of rod 26 and main body 34 of actuator 32 permits rod 26 to be unscrewed from actuator 32 and removed from tubular member 12 for cleaning. Main body 34 extends transversely to tubular member 12 through a longitudinal slot 36 in the sidewall of handle 18 and is integrally connected to a thumb grip 38 that slides within a longitudinal recess 40 in the outer surface of handle 18. Actuator 32, including main body 34 and thumb grip 38, is preferably made of a plastic material molded or machined in one piece. Main body 34 is somewhat shorter than slot 36, as viewed along the axis of tubular member 12, to permit actuator 32 to be reciprocated relative to tubular member 12. Distal end 44 of main body 34 of actuator 32 serves as a stop that abuts against the distal end of longitudinal slot 36 to limit axial movement of rod 26 and ball 28.

A screw 46 is threadedly received in proximal end 42 of main body 34, and a lock washer 48 and flat washer 50 are received between the head of screw 46 and main body 34. The head of screw 46 extends sufficiently in the proximal longitudinal direction such that the overall length of main body 34 and screw 46 exceeds the length of longitudinal slot 36 to prevent actuator 32 from escaping handle 18 when rod 36 is unscrewed from actuator 32 for cleaning. This arrangement prevents actuator 32 and coil spring 52, discussed below, from being lost inadvertently during cleaning of instrument 10.

A compression coil spring 52 is disposed about the proximal end of rod 26. One end of coil spring 52 bears on distal end 44 of main body 34 and the other end of coil spring 52 bears on an internal shoulder of tubular member 12 at the transition from larger inner diameter 22 to smaller inner diameter 24. Coil spring 52 is in compression and biases actuator 32, rod 26 and ball 28 in the proximal direction, i.e., ball 28 is urged in the direction toward handle 18.

Intermediate the proximal end 14 and the distal end 16 of instrument 10, an anteversion ring 54 is disposed about tubular member 12 in rotary sliding relationship such that anteversion ring 54 can be rotated through 360° about the longitudinal axis of tubular member 12. Anteversion ring 54 is prevented from moving axially toward distal end 16 by a washer 56 and a wave spring 58 that abuts against a radial flange 60 that extends from the outer surface of tubular member 12. Anteversion ring 54 is prevented from moving axially toward proximal end 14 by a washer 62 and a retaining ring 64 that is received in an annular groove in the outer surface of tubular member 12. Anteversion ring 54 includes a planar connector face 66 that is inclined at an angle of 40° relative to the longitudinal axis of tubular member 12 so as to face generally toward proximal end 14 or handle 18 of tubular member 12.

An anteversion rod 68 has a first leg 70 that extends perpendicularly from planar connector face 66 of anteversion ring 54, and has a second leg 72 that extends perpendicularly to first leg 70 and thus generally parallel to connector face 66. Second leg 72 extends generally toward distal end 16 of tubular member 12 at an angle of 40° to the longitudinal axis of tubular member 12.

Figure 2:
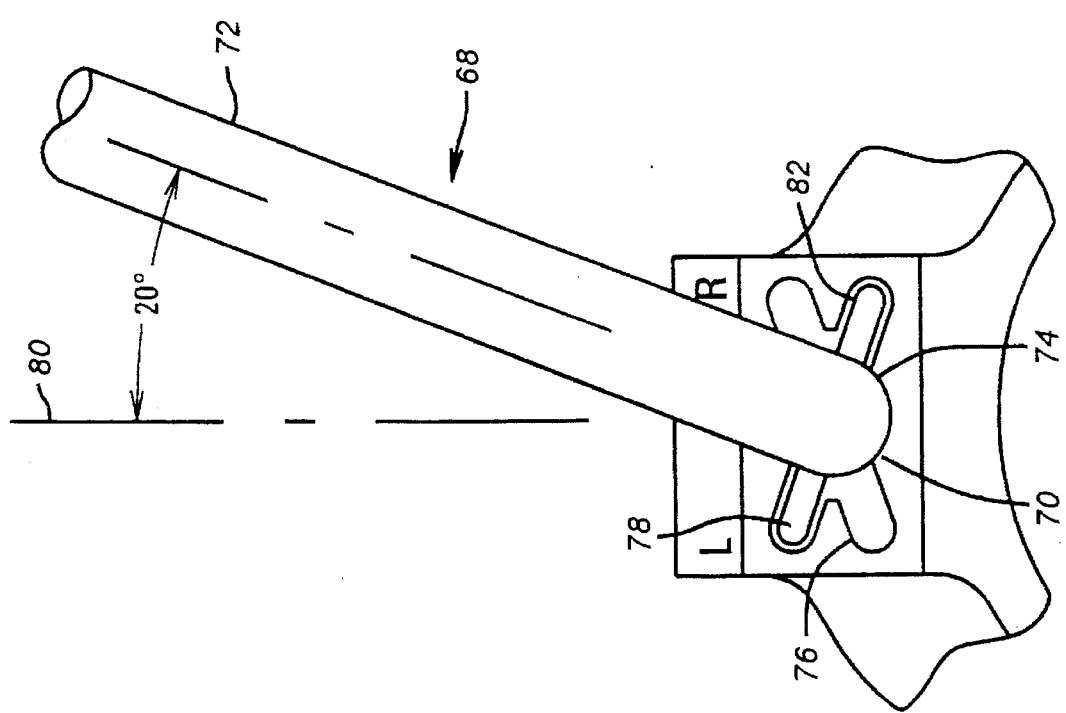
FIG. 2 is a fragmentary view of a portion of the instrument of FIG. 1.

Referring to FIG. 2, anteversion ring 54 is shown in a view normal to planar connector face 66. First leg 70 is received in a hole 74 in anteversion ring 54 oriented normal to connector face 66. Extending transversely from hole 74 are a pair of slots 76 and 78. Each slot 76 and 78 is disposed at an angle of 70° relative to the longitudinal axis 80 of tubular member 12, as measured from the right and left sides, respectively, of axis 80. A cross pin 82 is received through and fixed to first leg 70 of anteversion rod 68 in an orientation that is perpendicular to second leg 72. Cross pin 82 is shown received in slot 78 of anteversion ring 54 such that second leg 72 of anteversion rod 68 extends to the right of longitudinal axis 80 at an angle of 20° relative to axis 80. Alternately, cross pin 82 could be received in slot 76 such that second leg 72 would extend to the left of longitudinal axis 80 at an angle of 20° relative to axis 80.

Figure 3:
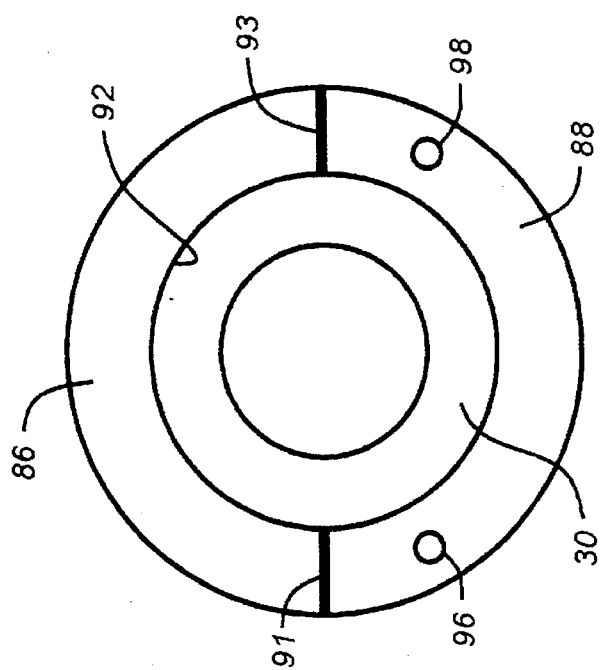
FIG. 3 is an end view of the instrument of FIG. 1.

Referring again to FIG. 1, and to FIG. 3, distal end 16 of instrument 10 includes a generally annular end face 84 divided into two semi-annular end faces 86 and 88 in different planes and having an common peripheral edge 90 and a common inner diameter 92. The equatorial diameter of ball 28 is somewhat less than inner diameter 92 to avoid interference therebetween. Semi-annular end face 86 lies in a plane perpendicular to the longitudinal axis of tubular member 12, and semi-annular end face 88 lies in a different plane that is offset distally from end face 86 but is also perpendicular to the longitudinal axis of tubular member 12. End faces 86 and 88 are connected by walls 91 and 93 that lie in a plane disposed diametrically across end face 84 and parallel to the longitudinal axis of tubular member 12.

Extending axially outwardly from semi-annular end face 88 are a pair of pins 96 and 98, which are symmetrically located relative to end face 88 such that an angle of 120° is subtended between pin 96 and pin 98.

Figure 4:
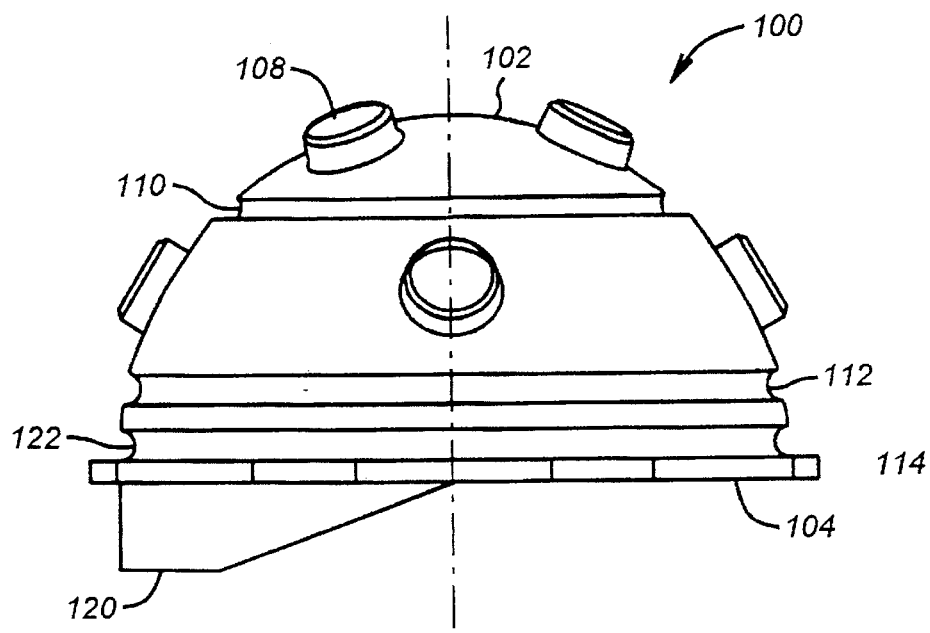
FIG. 4 is a side view of an acetabular cup with which the instrument of the present invention is useful.
Figure 5:
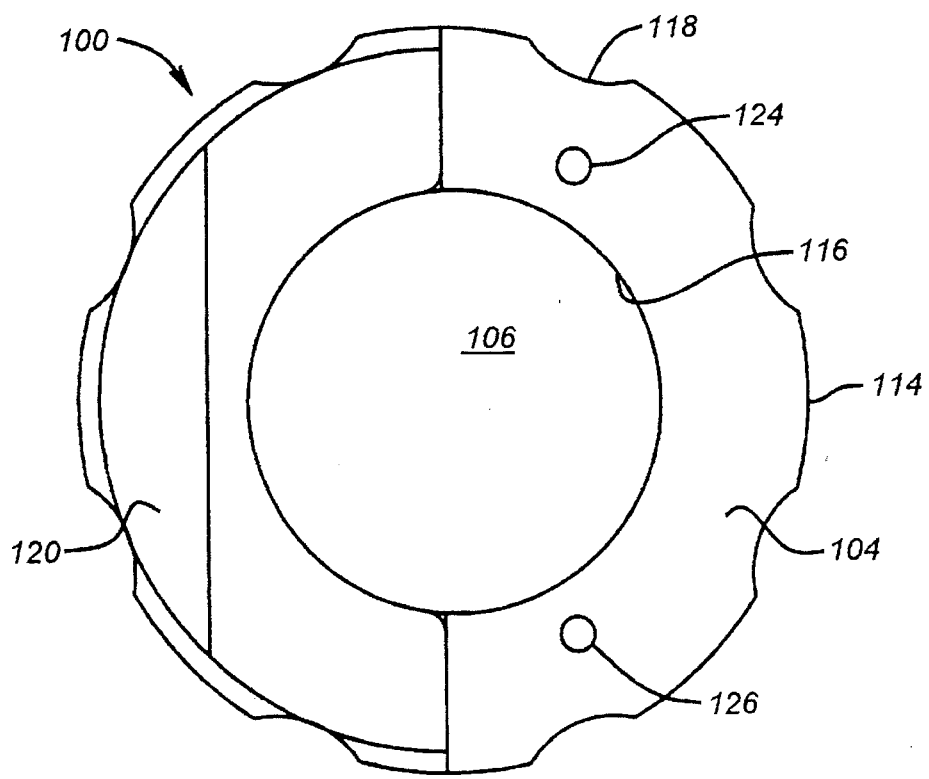
FIG. 5 is an end view of the acetabular cup of FIG. 4.
Figure 6:
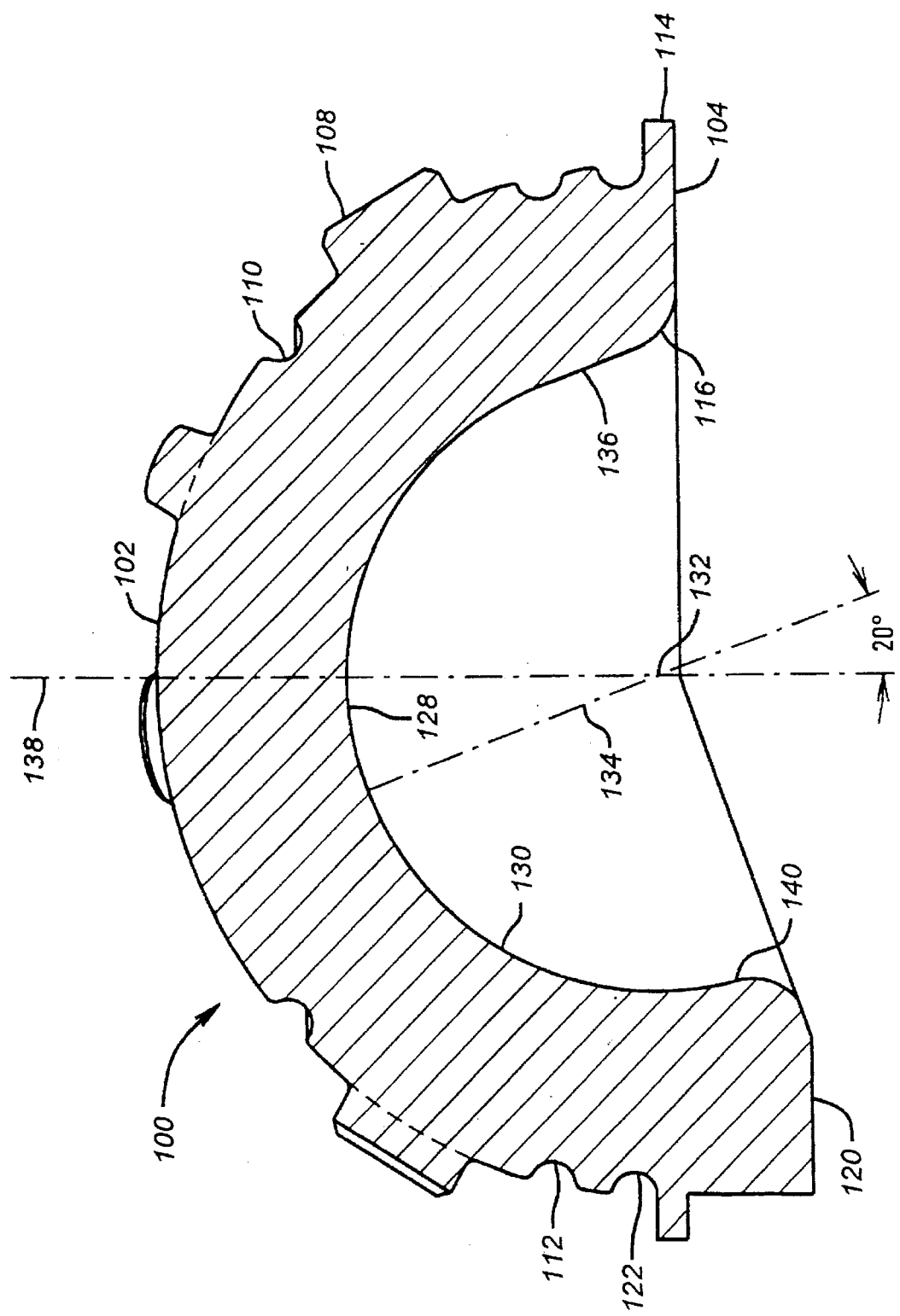
FIG. 6 is a cross-sectional view of the acetabular cup of FIG. 1.

Referring now to FIGS. 4, 5 and 6, there is illustrated an implantable acetabular cup 100 constructed entirely of high density polyethylene and intended for implantation with bone cement. Acetabular cup 100 is generally configured as a hemispherical cup having a spherical outer surface 102, a rim 104, and a cavity 106 for receipt of the head of a femoral component (not shown). Outer surface 102 of acetabular cup 100 has a plurality of round pegs 108 projecting normally from the surface thereof and distributed over the surface in spaced relationship. Outer surface 102 also includes a pair of annular grooves 110 and 112 oriented substantially parallel to rim 104. Pegs 108 and annular grooves 110 and 112 serve to interlock acetabular cup 100 with a cement mantel overlying outer surface 102 and disposed between acetabular cup 100 and the reamed acetabulum of the patient. Pegs 108 also act as cement spacers to position outer surface 102 at an appropriate distance from the reamed acetabulum such that the cement mantel is substantially uniform in thickness. Rim 104 includes a flange 114 extending radially outwardly from the opening 116 of acetabular cup 100 defined by the intersection of rim 104 and cavity 106. Flange 114 serves to retain and compress cement within the acetabulum as acetabular cup 100 is pressed in place, and is provided with a plurality of scalloped cut-outs 118 distributed evenly about the circumference of flange 114. Cut-outs 118 provide for the escape of excess bone cement extruded therethrough as acetabular cup 100 is pressed into the cement mantel in the acetabulum. Acetabular cup 100 also includes a hood 120 extending axially from rim 104 on only one side of opening 106. Hood 120 provides an extension of cavity 106 in a direction relative to the pelvis that is selected by the physician at the time of implantation. Outer surface 102 of acetabular cup 100 is also provided with an annular groove 122 immediately adjacent flange 114 on the cement receiving side of the flange. Annular groove 122 preferably receives an annular radiographically opaque marker therein to provide radiographic visibility to acetabular cup 100 which, because of its polyethylene construction, is otherwise radiographically transparent. The preferred radiographic marker is a tension coil spring (not shown) wound of stainless steel wire and joined at its ends to form a continuous ring. Such a radiographic marker is described in co-pending U.S. patent application Ser. No. 08/048,416, filed Apr. 14, 1993, and assigned to the assignee of the present invention, which application is hereby incorporated by reference.

Referring particularly to FIG. 5, rim 104 includes a pair of holes 124 and 126 therein which extend perpendicular to the plane of rim 104 and which are located on that portion of rim 104 that is opposite hood 120. Holes 124 and 126 are spaced apart such that an angle of 120° is subtended therebetween. Holes 124 and 126 are sized and located so as to receive pins 96 and 98 of instrument 10 therein, respectively, when rim 104 is placed in engagement with semi-annular end face 88 of instrument 10, as described below.

Referring particularly to FIG. 6, cavity 106 is defined by bearing surface 128 which includes a hemispherical portion 130 having a center 132 and an axis of rotation 134 that is inclined at an angle of 20° toward that side of acetabular cup 100 on which hood 120 is located. Indeed, the extension of hood 120 from the plane of rim 104 permits the full hemispherical portion 130 to exist, as otherwise the inclination of axis 134 would result in portion 130 extending beyond rim 104. A cylindrical portion 136 extends tangentially from hemispherical portion 130 on that side of acetabular cup 100 that is opposite hood 120. Cylindrical portion 136 shares axis 134 as its axis of rotation.

Acetabular cup 100 can be considered as having a polar axis 138 that passes through center 132 of hemispherical portion 130 and that is perpendicular to the plane of rim 104. When so considered, cavity 106 can also be considered as having an equator defined by the intersection of bearing surface 128 with a plane passing through center 132 and lying perpendicular to polar axis 138. The maximum radial excursion of portion 130, measured relative to polar axis 138, occurs at the equator. Because of the inclination of axis 134, a portion 140 of hemispherical portion 130 of bearing surface 128 lies below the equator as viewed in FIG. 6. Consequently, portion 140 is disposed radially inwardly of the maximum radial excursion of portion 130 relative to polar axis 138.

Figure 7:
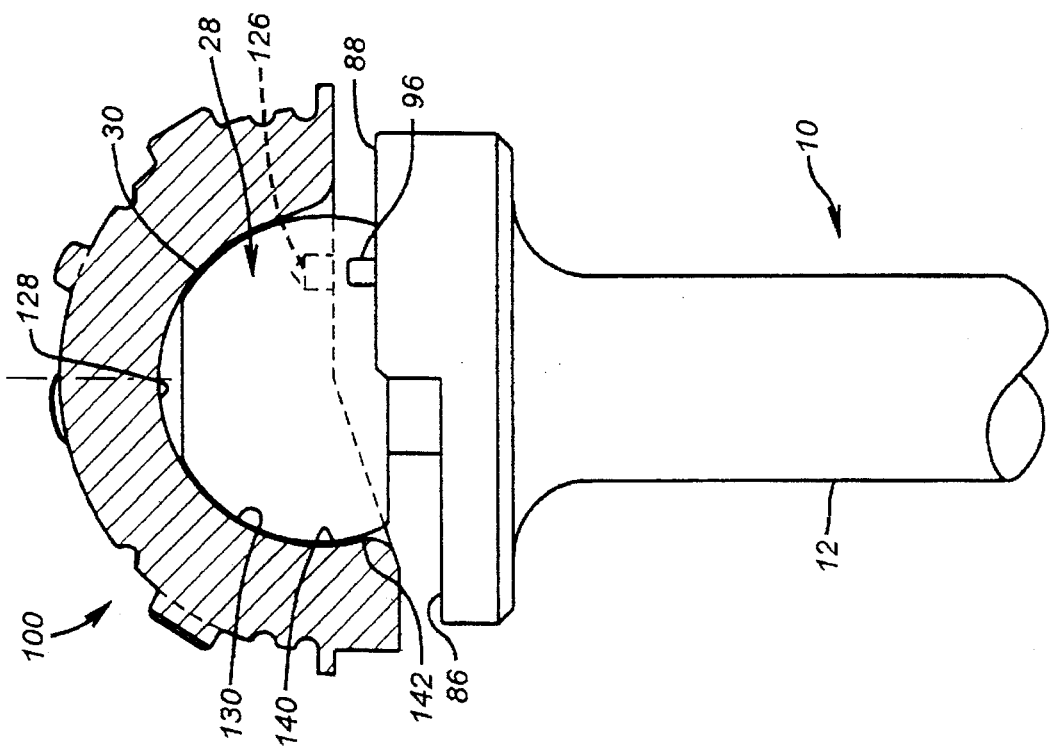
FIG. 7 is an enlarged partial view of the instrument of FIG. 4 shown in a first orientation in engagement with the acetabular cup of FIG. 4.

Referring now to FIG. 7, instrument 10 is shown in use relative to acetabular cup 100: Actuator 32 has been moved manually against the spring bias established by coil spring 52 to its maximally distal position, likewise moving ball 28 via rod 26 to its maximally distal position, resulting in ball 28 being displaced away from distal end 16 of instrument 10. The amount of displacement is at least as great as the distance that pins 96 and 98 extend beyond semi-annular end face 88, for reasons that will become apparent. While ball 28 is maintained in the displaced position, acetabular cup 100 is placed over ball 28 such that spherical surface 30 of ball 28 is received within cavity 106 of acetabular cup 100. Spherical surface 30 has a radius substantially the same as that of bearing surface 128 so that ball 28 engages bearing surface 128 in close fitting relationship. Acetabular cup 100 is oriented such that the plane of rim 104 is parallel to semi-annular end face 88, or in other words, such that the polar axis 138 of acetabular cup 100 is coaxial with the longitudinal axis of tubular member 12 of instrument 10. It should be noted that rim 104 is clear of pins 96 and 98, but that holes 124 and 126 are nevertheless axially aligned with pins 96 and 98. It should further be noted that ball 28 has its own equator at the maximum radial excursion of spherical surface 130 measured relative to the longitudinal axis of tubular member 12. The equator of ball 28 thus lies next adjacent and concentric with the equator of cavity 106 when acetabular cup 100 is placed on ball 28 as illustrated. Ball 28 also has a portion 142 that lies below its own equator and engages portion 140 of bearing surface 128.

Figure 8:
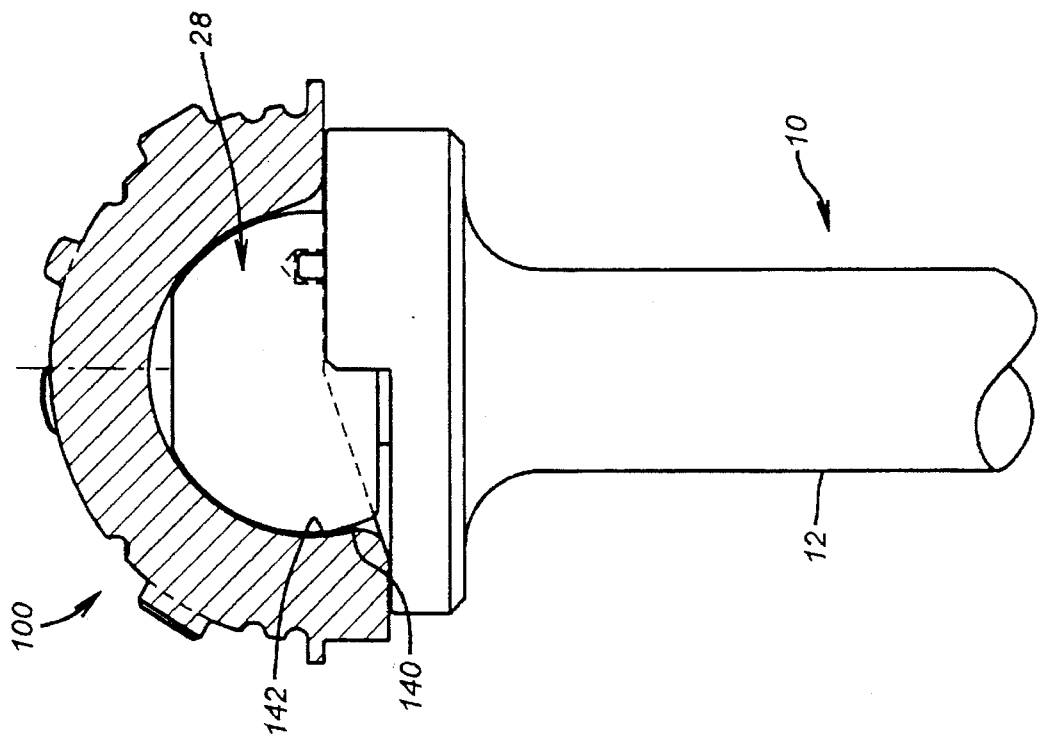
FIG. 8 is an enlarged partial view of the instrument of FIG. 1 shown in a second orientation in engagement with the acetabular cup of FIG. 4.

Referring now to FIG. 8, actuator 32 has been released and rod 26 and ball 28 have been allowed to move in the proximal direction toward handle 18 under the influence of coil spring 52. As ball 28 retracts toward tubular member 12, portion 142 of ball 28 bears against portion 140 of bearing surface 128 and draws acetabular cup 100 toward end face 84 of tubular member 12. As acetabular cup 100 so moves, holes 124 and 126 in rim 104 thereof engage and receive pins 96 and 98 of instrument 10. Portion 142 of ball 28 exerts a force against portion 140 of bearing surface 128 of acetabular cup 100 that has components extending radially outwardly relative to the longitudinal axis of tubular member 12 as well as axially toward tubular member 12. The radially outwardly directed force is opposed by pins 96 and 98 received within holes 124 and 126, such that lateral displacement of acetabular cup 100 relative to tubular member 12 is avoided. Consequently, the unopposed axial force having its source in coil spring 52 draws acetabular cup 100 tightly against tubular member 12 such that rim 104 engages semi-annular face 88 and hood 120 engages semi-annular face 86. Acetabular cup 100 is thus held securely to distal end 16 of instrument 10. It should be noted that since holes 124 and 126 and hood 120 are evenly spaced 120° apart from one another, the forces exerted by ball 28 and pins 96 and 98 are likewise evenly distributed so as to prevent distortion of acetabular cup 100.

Acetabular cup 100, when held by instrument 10 as illustrated in FIG. 8, can be cemented within the prepared acetabulum as follows. Assuming that the right hip is being replaced, and that the patient is lying on his left side, anteversion rod 68 is inserted into anteversion ring 54 in the orientation shown in FIG. 2 such that leg 72 of anteversion rod 68 extends to the right of instrument 10 as viewed from the proximal end 14 toward the distal end 16. Instrument 10 is then oriented such that first leg 70 of anteversion rod 68 is vertical, which results in the polar axis of acetabular cup 100 being adducted at an angle of 40°. Instrument 10 is further oriented such that second leg 72 of anteversion rod 68 is parallel to the axis of the patient. This is accomplished by pointing second leg 72 toward the back of the patient's right shoulder. This results in the polar axis of acetabular 100 being anteverted at an angle of 20°. While maintaining instrument 10 in this orientation, tubular member 10 can be rotated within anteversion ring 54 such that acetabular cup 100 is rotated about its own polar axis. The physician can therefor easily orient hood 120 of acetabular cup 100 in the desired orientation without disturbing the adduction and anteversion of cup 100.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

I claim:

1. A system comprising an acetabular cup and an instrument for holding said acetabular cup, said acetabular cup having a polar axis, and a rim lying in a plane generally perpendicular to said axis, said rim having at least one pin receiving hole therein located on a first side of a plane containing said polar axis and having a hood extending axially away from said rim on a second side of said plane containing said polar axis, said acetabular cup further having a concave generally spherical bearing surface therein open at said rim and defined at least in part by said hood, that portion of said bearing surface defined by said hood extending radially inwardly relative to said polar axis, said instrument having an elongate hollow tubular member having a proximal end and a distal end and a generally transverse end face at the distal end thereof;

at least one pin extending axially outwardly from said transverse end face;

an elongate rod;

said elongate hollow tubular member including means for supporting said elongate rod to permit axial movement of said elongate rod relative to said elongate hollow tubular member; and a ball attached to one end of said elongate rod proximate said transverse end face and moveable together with said elongate rod, said ball having a spherical surface for engaging at least that portion of said bearing surface defined by said hood that extends radially inwardly relative to said polar axis.

2. The system of claim 1, and further including a manually operable actuator connected to said rod for moving said rod axially relative to said tubular member.

3. The system of claim 2, and further including spring means for biasing said rod toward said proximal end of said tubular member.

4. The system of claim 1, in which said end face of said tubular member includes at least two portions offset axially from one another relative to the longitudinal axis of the tubular member.

5. The system of claim 4, in which said at least one pin extends from that offset portion of said end face that is more distal.

6. An instrument for holding an acetabular cup, comprising:

an elongate hollow tubular member having a proximal end and a distal end and a generally transverse end face at the distal end thereof;

at least one pin extending axially outwardly from said transverse end face;

an elongate rod;

said elongate hollow tubular member including means for supporting said elongate rod to permit axial movement of said elongate rod relative to said elongate hollow tubular member; and a ball attached to one end of said elongate rod proximate said transverse end face and moveable together with said elongate rod, said ball having a spherical surface, said spherical surface having a maximum radial excursion defining an equator, said equator defining an equatorial plane, and at least a portion of said spherical surface being disposed proximally of said equatorial plane.

7. The instrument of claim 6, and further including a manually operable actuator connected to said rod for moving said rod axially relative to said tubular member.

8. The instrument of claim 7, and further including spring means for biasing said rod toward said proximal end of said tubular member.

9. The system of claim 6, in which said end face of said tubular member includes at least two portions offset axially from one another relative to the longitudinal axis of the tubular member.

10. The instrument of claim 9, in which said at least one pin extends from that offset portion of said end face that is more distal.

* * * * *